(12) United States Patent
Kuo et al.

(10) Patent No.: US 11,459,614 B2
(45) Date of Patent: Oct. 4, 2022

(54) KITS FOR DIAGNOSING FRAGILE X SYNDROME AND USES THEREOF

(71) Applicant: Xiamen Biofast Biotechnology Co., Ltd., Xiamen (CN)

(72) Inventors: Yi-Yi Kuo, New Taipei (TW); Yu-Chiao Hsiao, New Taipei (TW); I-Fan Chiu, Hsinchu (TW); Lai-Ha Chung, New Taipei (TW); Shu-Ju Lee, New Taipei (TW)

(73) Assignee: XIAMEN BIOFAST BIOTECHNOLOGY CO., LTD., Xiamen (CN)

( * ) Notice: Subject to any disclaimer, the term of this patent is extended or adjusted under 35 U.S.C. 154(b) by 300 days.

(21) Appl. No.: 16/777,908

(22) Filed: Jan. 31, 2020

(65) Prior Publication Data
US 2020/0399699 A1 Dec. 24, 2020

(30) Foreign Application Priority Data
Jun. 24, 2019 (CN) .......................... 201910548848.0

(51) Int. Cl.
*C12P 19/34* (2006.01)
*C12Q 1/6883* (2018.01)
*C12Q 1/6806* (2018.01)

(52) U.S. Cl.
CPC ......... *C12Q 1/6883* (2013.01); *C12Q 1/6806* (2013.01); *C12Q 2600/158* (2013.01)

(58) Field of Classification Search
CPC .............................. C12Q 1/686; C12Q 1/6883
See application file for complete search history.

(56) References Cited

U.S. PATENT DOCUMENTS

2010/0243451 A1* 9/2010 Latham ................ C12Q 1/6858 204/450
2013/0115595 A1* 5/2013 Hantash ............... C12Q 1/6883 702/19

FOREIGN PATENT DOCUMENTS

CN 110157782 * 8/2019 ............. C12Q 1/686

OTHER PUBLICATIONS

Rychlik et al., Nucleic Acids Research 17(21), 8543-8551 (1989). (Year: 1989).*

* cited by examiner

*Primary Examiner* — Kenneth R Horlick (57) ABSTRACT

Disclosed herein is a method of performing polymerase chain reaction (PCR) to determine a repeating number of CGG sequence in fragile X mental retardation 1 (FMR1) gene. Also disclosed herein are a kit, and uses thereof in making a diagnosis of Fragile X syndrome (FXS) in a human subject based on the repeating number of the CGG sequence in a DNA sample isolated from the human subject. According to embodiments of the present disclosure, the kit comprises four primers, in which the first primer comprises a first polynucleotide sequence of SEQ ID NO: 1; the second primer comprises a second polynucleotide sequence of SEQ ID NO: 2; the third primer comprises a third polynucleotide sequence of SEQ ID NO: 3, and a non-human sequence disposed at and connected to the 5'-end of the third polynucleotide sequence; and the fourth primer comprises the non-human sequence.

10 Claims, 3 Drawing Sheets

Specification includes a Sequence Listing.

SEQUENCE LISTING

```
<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: synthesized_primer 1

<400> SEQUENCE: 1
cagctccgtt tcggtttcac ttcc                                          24

<210> SEQ ID NO 2
<211> LENGTH: 22
<212> TYPE: DNA
<213> ORGANISM: Artificial Sequence
<220> FEATURE:
<223> OTHER INFORMATION: synthesized_primer 2

<400> SEQUENCE: 2
agcgccattg gagccccgca ct                                            22

<210> SEQ ID NO 3
<211> LENGTH: 15
<212> TYPE: DNA
<213> ORGANISM: Artificial Sequence
<220> FEATURE:
<223> OTHER INFORMATION: synthesized_primer 3

<400> SEQUENCE: 3
cggcggcggc ggcgg                                                    15

<210> SEQ ID NO 4
<211> LENGTH: 20
<212> TYPE: DNA
<213> ORGANISM: Artificial Sequence
<220> FEATURE:
<223> OTHER INFORMATION: synthesized_nonhuman sequence 1

<400> SEQUENCE: 4
gcacgctcct gcacagcctc                                               20
```

-continued

<210> SEQ ID NO 5
<211> LENGTH: 23
<212> TYPE: DNA
<213> ORGANISM: Artificial Sequence
<220> FEATURE:
<223> OTHER INFORMATION: synthesized_nonhuman sequence 2

<400> SEQUENCE: 5
accgtctgcg cctcgttccg gct                                            23

<210> SEQ ID NO 6
<211> LENGTH: 28
<212> TYPE: DNA
<213> ORGANISM: Artificial Sequence
<220> FEATURE:
<223> OTHER INFORMATION: synthesized_primer P1

<400> SEQUENCE: 6
cgctcagctc cgtttcggtt tcacttcc                                       28

<210> SEQ ID NO 7
<211> LENGTH: 28
<212> TYPE: DNA
<213> ORGANISM: Artificial Sequence
<220> FEATURE:
<223> OTHER INFORMATION: synthesized_primer P2

<400> SEQUENCE: 7
gtagaaagcg ccattggagc cccgcact                                       28

<210> SEQ ID NO 8
<211> LENGTH: 41
<212> TYPE: DNA
<213> ORGANISM: Artificial Sequence
<220> FEATURE:
<223> OTHER INFORMATION: synthesized_primer P3

<400> SEQUENCE: 8
ctcgacgcac gctcctgcac agcctccggc ggcggcggcg g                        41

<210> SEQ ID NO 9
<211> LENGTH: 26
<212> TYPE: DNA
<213> ORGANISM: Artificial Sequence
<220> FEATURE:
<223> OTHER INFORMATION: synthesized_primer P4

<400> SEQUENCE: 9
ctcgacgcac gctcctgcac agcctc                                         26

<210> SEQ ID NO 10
<211> LENGTH: 40
<212> TYPE: DNA
<213> ORGANISM: Artificial Sequence
<220> FEATURE:
<223> OTHER INFORMATION: synthesized_primer P5

<400> SEQUENCE: 10
tgaccgtctg cgcctcgttc cggctcggcg gcggcggcgg                          40

<210> SEQ ID NO 11
<211> LENGTH: 25
<212> TYPE: DNA
<213> ORGANISM: Artificial Sequence
<220> FEATURE:
<223> OTHER INFORMATION: synthesized_primer P6

```
<400> SEQUENCE: 11
tgaccgtctg cgcctcgttc cggct                                    25

<210> SEQ ID NO 12
<211> LENGTH: 46
<212> TYPE: DNA
<213> ORGANISM: Artificial Sequence
<220> FEATURE:
<223> OTHER INFORMATION: synthesized_primer P7

<400> SEQUENCE: 12
gcacgctcct gcacagcctc ctcagctccg tttcggtttc acttcc             46

<210> SEQ ID NO 13
<211> LENGTH: 46
<212> TYPE: DNA
<213> ORGANISM: Artificial Sequence
<220> FEATURE:
<223> OTHER INFORMATION: synthesized_primer P8

<400> SEQUENCE: 13
gcacgctcct gcacagcctc agcgccattg gagcccgca cttcca              46

<210> SEQ ID NO 14
<211> LENGTH: 47
<212> TYPE: DNA
<213> ORGANISM: Artificial Sequence
<220> FEATURE:
<223> OTHER INFORMATION: synthesized_primer P9

<400> SEQUENCE: 14
accgtctgcg cctcgttccg gctcagctcc gtttcggttt cacttcc             47

<210> SEQ ID NO 15
<211> LENGTH: 48
<212> TYPE: DNA
<213> ORGANISM: Artificial Sequence
<220> FEATURE:
<223> OTHER INFORMATION: synthesized_primer P10

<400> SEQUENCE: 15
accgtctgcg cctcgttccg gctagcgcca ttggagcccc gcacttcc            48
```

KITS FOR DIAGNOSING FRAGILE X SYNDROME AND USES THEREOF

CROSS-REFERENCE TO RELATED APPLICATIONS

This application relates to and claims the benefit of China Application No. 201910548848.0, filed Jun. 24, 2019; the content of the application is incorporated herein by reference in its entirety.

BACKGROUND OF THE INVENTION

1. Field of the Invention

The present disclosure in general relates to the field of disease diagnosis. More particularly, the present disclosure relates to a kit comprising four primers with specific polynucleotide sequences, and uses of the kit in the diagnosis of Fragile X syndrome (FXS).

2. Description of Related Art

Fragile X syndrome (FXS) is a genetic condition caused by an abnormal expansion of CGG triplet repeat within the Fragile X mental retardation 1 (FMR1) gene, a gene located on the X chromosome. Normally, the FMR1 gene contains 5-44 repeats of the CGG triplet sequence. An FMR1 gene having 45-54 repeats of the CGG sequence is considered intermediate. The intermediate subjects usually do not exhibit any symptom of FXS or FMR1-related disorders. The subjects having 55-200 repeats of the CGG sequence are defined as having a premutation. Most people with a premutation are intellectually normal. However, in some cases, the subjects with a premutation may exhibit mild physical symptoms of FXS (such as protruding ears), and emotional problems (such as anxiety or depression). Besides, the premutation is also associated with an increased risk of different physical and psychiatric disorders, including fragile X-associated primary ovarian insufficiency (FXPOI), fragile X-associated tremor/ataxia syndrome (FXTAS), and fragile X-associated neuropsychiatric disorder (FXAND). The FXS patients known as having a full mutation of FXS gene comprise more than 200 repeats of the CGG triplet. It is known that the overextension of the CGG triplet repeat results in the shortage or deficiency of FMRP protein (the protein encoded by the FMR1 gene) that leads to the disruption of nervous system. In addition to intellectual disability, the conditions or disorders associated with FSX also include, autism, social anxiety, attention deficit hyperactivity disorder (ADHD), attention deficit disorder (ADD), strabismus, impulsivity, and seizure. Further, most FXS patients have characteristic physical features, such as a long and narrow face, large ears, a prominent jaw and forehead, unusually flexible fingers, flat feet, soft skin, and hypotonia.

The mainstream methodology for the diagnosis of FXS includes Southern blot analysis and polymerase chain reaction (PCR). However, Southern blot analysis is a costly and time consuming procedure that requires large amount of deoxyribonucleic acid (DNA) samples. Regarding PCR, it's accuracy is limited by the undenaturable secondary structure due to high CG contents of the DNA sample. Besides, both two methodologies fail to define the precise number of the CGG triplet repeat, and accordingly, not being able to distinguish between different types of alleles, especially, between the premutation and full mutation alleles, or between the normal and full mutation alleles.

In view of the foregoing, there exists in the related art a need for an improved method for determining the repeating number of the CGG triplet in a subject in a more accurate and efficient manner so as to determine whether such the subject has FXS (i.e., having more than 200 repeats) or is a carrier of FXS (i.e., having 55-200 repeats).

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method of performing polymerase chain reaction (PCR) to determine a repeating number of the sequence of CGG in FMR1 gene by amplifying a CGG repeat region of the FMR1 gene via a first to a fourth primers. According to embodiments of the present disclosure, the first primer comprises a first polynucleotide sequence, which is complementary to the upstream sequence of the CGG repeat region; the second primer comprises a second polynucleotide sequence, which is complementary to the downstream sequence the CGG repeat region; the third primer comprises a third polynucleotide sequence, and a non-human sequence disposed at and connected to the 5'-end of the third polynucleotide sequence, wherein the third polynucleotide sequence is complementary to the CGG repeat region; and the fourth primer comprises the non-human sequence. According to some working examples, the third polynucleotide sequence comprises a repeating sequence of CGG, GGC, GCG, CCG, GCC, and/or CGC.

According to some preferred embodiments, in the PCR, the concentration of the third primer is at least 1,000-fold lower than the concentration of each of the first, second, and fourth primers.

The second aspect of the present disclosure pertains to a kit for performing the PCR process thereby making a diagnosis as to whether a human subject has Fragile X syndrome (FXS) or is a carrier of FXS. The kit comprises four primers, and polymerase chain reaction (PCR) reagents, which optionally comprise DNA polymerase, buffer, $MgCl_2$, deoxynucleotide triphosphates (dNTPs), betaine, ethylene glycol, and glycerol.

According to embodiments of the present disclosure, the first primer comprises a first polynucleotide sequence of SEQ ID NO: 1; the second primer comprises a second polynucleotide sequence of SEQ ID NO: 2; the third primer comprises a third polynucleotide sequence of SEQ ID NO: 3, and a non-human sequence disposed at and connected to the 5'-end of the third polynucleotide sequence; and the fourth primer comprises the non-human sequence.

According to some embodiments of the present disclosure, the non-human sequence comprises the polynucleotide sequence of SEQ ID NO: 4. In the case of these embodiments, the first primer has the polynucleotide sequence of SEQ ID NO: 6; the second primer has the polynucleotide sequence of SEQ ID NO: 7; the third primer has the polynucleotide sequence of SEQ ID NO: 8; and the fourth primer has the polynucleotide sequence of SEQ ID NO: 9.

Alternatively, the first primer further comprises the non-human sequence disposed at the 5'-end of the first polynucleotide sequence, and the second primer further comprises the non-human sequence disposed at and connected to the 5'-end of the second polynucleotide sequence. According to some alternative embodiments of the present disclosure, the first primer has the polynucleotide sequence of SEQ ID NO: 12; the second primer has the polynucleotide sequence of SEQ ID NO: 13; the third primer has the polynucleotide sequence of SEQ ID NO: 8; and the fourth primer has the polynucleotide sequence of SEQ ID NO: 9.

According to certain embodiments of the present disclosure, the non-human sequence comprises the polynucleotide sequence of SEQ ID NO: 5. In the case of these embodiments, the first primer has the polynucleotide sequence of SEQ ID NO: 6; the second primer has the polynucleotide sequence of SEQ ID NO: 7; the third primer has the polynucleotide sequence of SEQ ID NO: 10; and the fourth primer has the polynucleotide sequence of SEQ ID NO: 11.

Alternatively, the first primer further comprises the non-human sequence disposed at and connected to the 5'-end of the first polynucleotide sequence, and the second primer further comprises the non-human sequence disposed at and connected to the 5'-end of the second polynucleotide sequence. According to some alternative embodiments of the present disclosure, the first primer has the polynucleotide sequence of SEQ ID NO: 14; the second primer has the polynucleotide sequence of SEQ ID NO: 15; the third primer has the polynucleotide sequence of SEQ ID NO: 10; and the fourth primer has the polynucleotide sequence of SEQ ID NO: 11.

Optionally, the second primer is conjugated with a reporter molecule.

Optionally, the present kit further comprises three DNA templates serving as positive controls, and/or one DNA template serving as a negative control. According to some working examples of the present disclosure, the DNA templates serving as the positive controls respectively have 10-44, 45-54, and 55-200 repeats of the sequence of CGG within the polynucleotide sequences thereof, and the DNA template serving as the negative control does not have the sequence of CGG within the polynucleotide sequence thereof.

Another aspect of the present disclosure pertains to a method of making a diagnosis as to whether a human subject has FXS or is a carrier of FXS by using the kit according to any embodiment or example of the present disclosure. The method comprises the steps of, (a) extracting a DNA sample from the human subject;
(b) mixing the DNA sample with the first to fourth primers in the PCR reagents;
(c) subjecting the mixture of the step (b) to PCR;
(d) determining a repeating number of the sequence of CGG in the product of the step (c); and
(e) making a diagnosis of FXS based on the repeating number determined by the step (d), wherein the repeating number of 201-375 indicates that the human subject has the FXS, and the repeating number of 55-200 indicates that the human subject is the carrier of the FXS.

According to certain embodiments of the present disclosure, in the mixture of the step (b), the concentration of the third primer is at least 1,000-fold lower than the concentration of each of the first, second, and fourth primers. In one specific example, the concentration of the third primer is 0.1-0.5 nM, and the concentration of each of the first, second, and fourth primers is 0.5-1 µM.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "polynucleotide sequence" is understood to mean either a double-stranded DNA or a single-stranded DNA. The polynucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

The term "repeating sequence" when made in reference to a nucleotide sequence (e.g., CGG, GGC, GCG, CCG, GCC, or CGC) that is contained in a polynucleotide sequence (e.g., the third polynucleotide sequence of the present disclosure) means that the nucleotide sequence is reiterated from 1 to 10 times (for example, reiterating 1, 2, 3, 4, 5, 6, 7, 8, 9, or 10 times) in the polynucleotide sequence. The repeats of the nucleotide sequence may be non-contiguous or contiguous. The term "non-contiguous" when made in reference to a repeating nucleotide sequence means that at least one nucleotide (or nucleotide analog) is placed between the repeating sequences. The term "contiguous" when made in reference to a repeating nucleotide sequence means that there is no intervening nucleotide (or nucleotide analog) between the repeating sequences.

The term "CGG repeat region" as used herein refers to a region of FMR1 gene, in which at least two repeats of the CGG sequence are contained in the region, in which each CGG sequence and its next CGG sequence may be contiguous (i.e., no intervening nucleotide is present between two CGG sequences) or non-contiguous (i.e., one or more nucleotides are present between two CGG sequences) to each other. According to some embodiments, each CGG sequence and its next CGG sequence form a contiguous sequence without any intervening nucleotide placed therebetween.

As used herein, the term "complementary" refers to the natural binding of polynucleotides under permissive salt and temperature conditions by base-pairing. The binding between polynucleotides are typically formed by hydrogen bonds between nucleotide units in antiparallel polynucleotide, strands or regions. Complementary polynucleotide strands or regions can base pair in the Watson-Crick manner (e.g., A to T, A to U, or C to G), or in any other manner that allows for the formation of stable duplexes. For example, the nucleotide sequence "AGT" binds to the complementary sequence "TCA". Complementarity between two single-stranded molecules may be "partial", in which only some of the nucleic acids bind, or it may be complete when total complementarity exists between the single stranded molecules.

The term "diagnosis" as used herein refers to methods by which a skilled artisan can estimate and/or determine the probability ("a likelihood") of whether or not a patient is suffering from a given disease or condition. In the case of the present invention, "diagnosis" includes using the PCR product amplified by the four primers of the present kit, optionally together with other clinical characteristics, to arrive at a diagnosis (that is, the occurrence or nonoccurrence) of FXS for the subject from which a DNA sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

As used herein, the term "non-human" refers to any animal other than the human species, from whom a sequence (i.e., the non-human sequence of the third primer of the present kit) is obtained (i.e., directly cloning from the non-human animal without any modification) or derived (i.e., cloning from the non-human animal with one or more modifications; such as, replacement or deletion of one or more nucleic acids of the sequence). The non-human animals suitable for obtaining or deriving the present non-human sequence include, but are not limited to, mouse, rat, hamster, guinea pig, rabbit, pig, monkey, sheep, goat, horse, cat, dog, chimpanzee, ape, orangutan, wolf, deer, donkey, zebra, bear, giraffe, lion, and tiger. According to some embodiments of the present disclosure, the non-human sequence of the present kit is derived from bacteriophage without sequence modification.

As used herein, the term "PCR reagents" refers to the chemicals, apart from the specified primers (i.e., the first to the fourth primers of the present kit), needed to perform the PCR process. These chemicals generally comprise four classes of components: (i) an aqueous buffer (also known as PCR buffer), (ii) a water soluble magnesium salt (e.g., $MgCl_2$), (iii) at least four deoxyribonucleotide triphosphates (dNTPs, including thymidine triphosphate (dTTP), deoxyadenosine triphosphate (dATP), deoxycitidine triphosphate (dCTP) and deoxyguanosine triphosphate (dGTP)), and (iv) a polynucleotide polymerase, preferably a DNA polymerase, more preferably a thermostable DNA polymerase, i.e., a DNA polymerase, which can tolerate temperatures between 90° C. and 100° C. for a total time of at least 10 minutes without losing more than about half its activity. Depending on desired purposes, these chemicals may comprise additional components for improving the efficacy and/or specificity of the PCR process, such as betaine, ethylene glycol, and glycerol.

The term "subject" refers to a human species diagnosed by the kit and/or method of the present invention. The term "subject" is intended to refer to both the male and female gender unless one gender is specifically indicated.

II. Description of the Invention

The present disclosure aims at providing a method of performing PCR to determine a repeating number of the sequence of CGG in FMR1 gene by amplifying a CGG repeat region of the FMR1 gene via a first to a fourth primers. Also disclosed herein are a kit and a method for accurately and efficiently diagnosing whether a human subject has Fragile X syndrome (FXS), or is a carrier of FXS based on the repeating number of the CGG sequence in FMR1 gene, so that a clinical practitioner or a skilled artisan may administer to a FXS patient a suitable treatment in time, and providing a genetic counseling to a FXS carrier with risk assessment thereby reducing or preventing maternal transmission.

As mentioned above, FXS is caused by an abnormal expansion of CGG repeats in the 5'-untranslated region of the FMR1 gene. Thus, the kit of the present disclosure is characterized in having four primers, in which the first and second primers respectively comprise a first and a second polynucleotide sequences complementary to the upstream and downstream sequences of the CGG repeats (i.e., the CGG repeat region); the third primer comprises a third polynucleotide sequence complementary to the sequence of the CGG repeats, and a non-human sequence disposed at and connected to the 5'-end of the third polynucleotide sequence; and the fourth primer comprises the same non-human sequence as the third primer. In practice, the first, third, and fourth primers respectively serve as forward primers, which in combination with the second primer that serves as a reverse primer, may amplify different lengths of DNA fragments from a DNA sample. Specifically, the first and second primers are useful in amplifying a first DNA fragment via binding to the upstream and downstream sequences of the CGG repeats; the polynucleotide sequence of the thus-obtained first DNA fragment thus contains, in sequence, the upstream sequence of CGG repeats, the sequence of CGG repeats, and the downstream sequence of CGG repeats. The third and second primers are employed to amplify a plurality of second DNA fragments via respectively binding to the CGG repeats and the downstream sequences of the CGG repeats; the polynucleotide sequences of the thus-obtained second DNA fragments thus contain, in sequence, the non-human sequence, the sequence of CGG repeats, and the downstream sequence of CGG repeats. The fourth and second primers are used to further amplify the second fragments obtained by the third and second primers via respectively binding to non-human sequence and the downstream sequence of CGG repeats of the second DNA fragments. In this way, a skilled artisan may decide the repeating number of the CGG sequence by an electrophoresis assay (e.g., a capillary electrophoresis assay) via comparing the size of the first fragment to at least two control fragments respectively having known molecular sizes and CGG repeating numbers (e.g., one control fragment having 55 CGG repeats, and another control fragment having 200 CGG repeats). The second fragments form stutter peaks in the electropherogram; accordingly, a skilled artisan may determine the absence or presence of a mutation in the FMR1 gene (e.g., the abnormal expansion of the CGG repeats, and/or the an AGG sequence in the CGG repeats) by detecting the stutter peaks, in which the presence of the stutter peaks indicates that the CGG repeats of the FMR1 gene comprise the mutation.

More specifically, based on the fact that FXS is a X-linked condition, the male subject (having one X chromosome, and one Y chromosome; i.e., X/Y pairing) without a mutation in the CGG repeats would exhibit one main peak in the electropherogram, i.e., the main peak formed by the first DNA fragment amplified from the X chromosome thereof. In the case when the subject is a male having FXS, then one main peak and several stutter peaks (i.e., the minor peaks formed by the second DNA fragments having different numbers of CGG repeats) would appear in the electropherogram. Alternatively, the subject may be a female having two X chromosomes, i.e., X/X paring. In this case, when the female has normal or intermediate alleles (i.e., alleles having CGG repeating numbers <55), then one or two main peaks would be presented in the electropherogram. In short, the presence of one main peak indicates that two first DNA fragments respectively amplified from two X chromosomes of the female have a size difference less than the resolution of the electropherogram; for example, one DNA fragment having 29 repeats of the CGG sequence, and the other DNA fragment having 30 repeats of the CGG sequence. On the other hand, the presence of two mains peaks indicates that two first DNA fragments respectively amplified from two X chromosomes of the female have a size difference greater than the resolution of the electropherogram; for example, one DNA fragment having 29 repeats of the CGG sequence, and the other DNA fragment having 54 repeats of the CGG sequence. In the case when the subject is a female having FXS or being a FXS carrier, then two main peaks and several stutter peaks disposed between the two main peaks would appear in the electropherogram.

According to optional embodiments of the present disclosure, the kit further comprises three DNA templates serving as positive controls, in which each of the three DNA templates has a CGG repeating number different from one another. After conducting the PCR process with the four primers of the present kit and analyzed by a detection technique (e.g., a capillary electrophoresis assay), a calibration plot may be constructed, in which the x-coordinate corresponds to the repeating number of the CGG sequence in the DNA template, and the y-coordinate corresponds to the molecular size of the DNA template. The CGG repeating number of the DNA sample are accordingly determined from the calibration plot based on the molecular size thereof. According to some working examples of the present disclosure, the first to the third DNA templates respectively have 10-44, 45-54, and 55-200 repeats of the sequence of CGG within the polynucleotide sequences thereof. In one specific example, the kit comprises seven DNA templates, which respectively have 10, 29, 36, 54, 85, 120, and 142 repeats of the sequence of CGG within the polynucleotide sequences thereof. As would be appreciated, the number of DNA templates, and the CGG repeating number of each DNA template should not be limited to the embodiment and example illustrated herein. Any DNA template having a specific number of the CGG repeats may be employed as the DNA template for constructing the calibration plot.

Optionally, the present kit further comprises a DNA template serving as a negative control, in which the DNA template does not have the sequence of CGG within the polynucleotide sequence thereof.

According to some embodiments of the present disclosure, the first primer comprises a first polynucleotide sequence of SEQ ID NO: 1; the second primer comprises a second polynucleotide sequence of SEQ ID NO: 2; the third primer comprises a third polynucleotide sequence of SEQ ID NO: 3, and a non-human sequence comprising the polynucleotide sequence of SEQ ID NO: 4; and the fourth primer comprises the polynucleotide sequence of SEQ ID NO: 4. According to alternative embodiments of the present disclosure, the first primer comprises a first polynucleotide sequence of SEQ ID NO: 1; the second primer comprises a second polynucleotide sequence of SEQ ID NO: 2; the third primer comprises a third polynucleotide sequence of SEQ ID NO: 3, and a non-human sequence comprising the polynucleotide sequence of SEQ ID NO: 5; and the fourth primer comprises the polynucleotide sequence of SEQ ID NO: 5. It is noted that the fourth primer should comprise the same non-human sequence as the third primer, so that it may be used to further augment the DNA fragments (e.g., the second DNA fragments as mentioned above) amplified by the third primer. As would be appreciated, the polynucleotide sequence of the non-human sequence should not be limited to the SEQ ID NO: 4 or 5 illustrated herein. Instead, any non-human sequence satisfying the functional requirement (i.e., the third and fourth primers comprising the same non-human sequence for amplifying the same DNA fragment in the PCR process) may serve as the non-human sequence for constructing the third and fourth primers of the present kit.

According to some embodiments of the present disclosure, the non-human sequence comprises the polynucleotide sequence of SEQ ID NO: 4, in which the first primer has the polynucleotide sequence of SEQ ID NO: 6; the second primer has the polynucleotide sequence of SEQ ID NO: 7; the third primer has the polynucleotide sequence of SEQ ID NO: 8; and the fourth primer has the polynucleotide sequence of SEQ ID NO: 9.

According to alternative embodiments, the non-human sequence comprises the polynucleotide sequence of SEQ ID NO: 4, in which in addition to the first and second polynucleotide sequences, the first primer further comprises the non-human sequence disposed at the 5'-end of the first polynucleotide sequence, and the second primer further comprises the non-human sequence disposed at and connected to the 5'-end of the second polynucleotide sequence. In some specific examples, the first primer has the polynucleotide sequence of SEQ ID NO: 12; the second primer has the polynucleotide sequence of SEQ ID NO: 13; the third primer has the polynucleotide sequence of SEQ ID NO: 8; and the fourth primer has the polynucleotide sequence of SEQ ID NO: 9.

According to certain embodiments of the present disclosure, the non-human sequence comprises the polynucleotide sequence of SEQ ID NO: 5, in which the first primer has the polynucleotide sequence of SEQ ID NO: 6; the second primer has the polynucleotide sequence of SEQ ID NO: 7; the third primer has the polynucleotide sequence of SEQ ID NO: 10; and the fourth primer has the polynucleotide sequence of SEQ ID NO: 11.

Alternatively, the first and second primers may respectively have the non-human sequence disposed at and connected to the 5'-ends of the first and second polynucleotide sequences, in which the non-human sequence comprises the polynucleotide sequence of SEQ ID NO: 5. In some specific examples, the first primer has the polynucleotide sequence of SEQ ID NO: 14; the second primer has the polynucleotide sequence of SEQ ID NO: 15; the third primer has the polynucleotide sequence of SEQ ID NO: 10; and the fourth primer has the polynucleotide sequence of SEQ ID NO: 11.

Optionally, for the detection purpose, the second primer has a reporter molecule conjugated at the 5'-end or 3'-end. Non-limiting examples of reporter molecule suitable to be conjugated with the second primer include, but are not limited to, a fluorescent molecule, a luminescent molecule, a phosphorescent molecule, a colorimetric dye, a contrast agent, and an enzyme.

According to embodiments of the present disclosure, in addition to the four primers described above, the present kit further comprises PCR reagents for amplifying DNA segments in PCR assay. In certain examples, the PCR reagents comprise DNA polymerase, PCR buffer (e.g., Tris(hydroxymethyl)aminomethane buffer (Tris buffer), Tris-HCl buffer, or any aqueous buffer known by skilled artisan for conducting the PCR process), $MgCl_2$, deoxynucleotide triphosphates (dNTPs, including dATP, dTTP, dGTP, and dCTP), betaine, ethylene glycol, and glycerol.

Also disclosed herein is a method for making a diagnosis as to whether a human subject has FXS or is a carrier of FXS by using the kit in accordance with any embodiment or example of the present disclosure. The present method comprises the steps of, (a) extracting a DNA sample from the human subject;
(b) mixing the DNA sample with the first to fourth primers in the PCR reagents;
(c) subjecting the mixture of the step (b) to PCR;
(d) determining a repeating number of the sequence of CGG in the product of the step (c); and
(e) making a diagnosis of FXS based on the repeating number determined by the step (d), wherein the repeating number of greater than 200 indicates that the human subject has the FXS, and the repeating number of 55-200 indicates that the human subject is the carrier of the FXS.

In the step (a), a DNA sample is extracted from a cell or tissue of the human subject. The cell or tissue may be any available cell or tissue obtained from the human subject, as long as such the cell or tissue contains the DNA of the human subject. For example, the cell may be an epithelial cell, fibroblast, stem cell, blood cell, keratinocyte, or adipocyte. The tissue may be a tissue biopsy, such as a gastric, esophageal, colorectal, brain, hepatic, splenic, or skin biopsy. According to one example of the present disclosure, the DNA sample was extracted from the blood sample of the human subject. The DNA sample may be extracted from the cell or tissue by a commercial kit, or any conventional DNA extraction technique; for example, the phenol/chloroform assay, and detergent (e.g., sodiumdodecyl sulfate, Tween-20, NP-40, and Triton X-100)/acetic acid assay.

Then, the extracted DNA sample is mixed with the present PCR reagents containing the first to the fourth primers, followed by PCR amplification as respectively illustrated in the steps (b) and (c). According to some embodiments of the present disclosure, the final concentration of the third primer in the PCR reagents is at least 1,000-fold lower than the final concentration of each of the first, second, and fourth primers in the PCR reagents. In one specific example, the final concentration of the third primer is 0.1-0.5 nM, and the final concentration of each of the first, second, and fourth primers is 0.5-1 µM.

In the step (d), the repeating number of the CGG sequence in the PCR product of the step (c) is determined. Depending on desired purposes, the repeating number of the CGG sequence may be determined by a gene sequencing assay, an electrophoresis assay (e.g., agarose gel electrophoresis, or capillary electrophoresis assay), or an immunological assay. According to some embodiments of the present disclosure, the molecular size of the DNA fragment (e.g., the first DNA fragment described above) amplified by the PCR process is first analyzed by a capillary electrophoresis assay, and then, the repeating number of the CGG sequence in the DNA fragment is determined by comparing the molecular size of the DNA fragment to at least two control fragments respectively having known molecular sizes and CGG repeating numbers (e.g., one control fragment having 55 CGG repeats, and another control fragment having 200 CGG repeats). Alternatively, the repeating number of the CGG sequence in the DNA fragment may be determined by the calibration plot constructed by the DNA templates of the present kit, in which the x-coordinate of the calibration plot corresponds to the repeating number of the CGG sequence, and the y-coordinate of the calibration plot corresponds to the molecular size. Accordingly, the CGG repeating number of the DNA sample may be determined from the calibration plot based on the molecular size thereof. In the preferred embodiments, the CGG repeating number of the DNA sample is determined from the calibration plot constructed by DNA templates respectively having 10, 29, 36, 54, 85, 120, and 142 CGG repeats in their polynucleotide sequences.

Next, in the step (e), a clinical practitioner or a skilled artisan may make a diagnosis of FXS based on the repeating number as determined in the step (d). According to some embodiments of the present disclosure, when the CGG repeating number of the DNA sample is equal to or lower than 44 (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44), then the human subject is a normal subject. In the case when the CGG repeating number of the DNA sample ranges between 45 to 54 (e.g., 45, 46, 47, 48, 49, 50, 51, 52, 53, or 54), then the human subject has an intermediate allele of the FMR1 gene. In the case when the CGG repeating number of the DNA sample ranges between 55 to 200 (e.g., 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200), then the human subject is a FXS carrier. When the CGG repeating number of the DNA sample is greater than 200 (e.g., 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400 or more), then the human subject has FXS. According to some embodiments, when the repeating number ranges between 201 and 375 (e.g., 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, or 375), then the human subject has FXS. In one specific example, when the repeating number ranges between 201 and 371, then the human subject has FXS.

The present diagnostic kit and method are advantageous in at least the four following aspects:

(1) The first and the second primers are useful in amplifying the 5'-untranslated region of the FMR1 gene (i.e., the first DNA fragment as described above), and the second to the fourth primers are useful in amplifying the CGG sequence of the FMR1 gene (i.e., the second DNA fragments as described above). After the analysis of a detection technique (e.g., a capillary electrophoresis assay), a skilled artisan may determine the allele type of the FMR1 gene via detecting the profiles of the main and stutter peaks respectively formed by the first and second DNA fragments thereby diagnosing whether a subject has FXS or is a FXS carrier.

(2) The difference between the concentration of the third primer and each concentration of first, second and fourth primers in operation ensures that the PCR process may amplify the first and second DNA fragments is a more specific manner so that different allele types (for example, the premutation and full mutation alleles, or the normal and full mutation alleles) may be accurately determined.

(3) In the case when the positive controls (i.e., the DNA templates for constructing the calibration plot) are provided in the present kit, a skilled artisan may accurately determine the repeating number of the CGG sequence based on the calibration plot constructed by the positive controls. According to a specific example, the DNA templates respectively having 10, 29, 36, 54, 85, 120, and 142 repeats of the CGG sequence, which cover the normal allele (i.e., 10 and 29 repeats), intermediate allele (i.e., 36 and 54 repeats), and permutation allele (i.e., 85, 120 and 124 repeats) provides a useful means to reduce errors in the determination of the CGG repeating number.

(4) Compared to conventional methodology, which takes a lot of time for the analytic process and requires large amount of DNA samples, 2.5 ng/µl of DNA sample is sufficient to be analyzed by the present kit and method, and the analytic process may be accomplished in 6 hours.

Based on the diagnostic result, a clinical practitioner or a skilled artisan may administer to a FXS patient a suitable treatment in time thereby relieving symptoms associated with FXS. Alternatively, in the case when the subject is diagnosed as a FXS carrier, then a genetic counseling and management options available are provided.

Accordingly, another aspect of the present disclosure pertains to a method of treating a human subject having FXS. The method comprises, (a) extracting a DNA sample from the human subject;
(b) mixing the DNA sample with the first to fourth primers in the PCR reagents of the present disclosure;
(c) subjecting the mixture of the step (b) to PCR;
(d) determining a repeating number of the sequence of CGG in the product of the step (c); and
(e) treating the human subject having the FXS based on the repeating number determined by the step (d), wherein when the human subject has the repeating number of 201-375, then administering to the human subject an effective amount of a therapeutic agent.

The steps (a) to (d) of the therapeutic method are quite similar to those aforementioned, and hence, detailed description thereof is omitted herein for the sake of brevity.

In the step (e), a therapeutic agent is administered to the human subject having FXS so as to alleviate or ameliorate the symptoms associated with FXS. Examples of the therapeutic agent include, but are not limited to, antidepressant (e.g., paroxetine, citalopram, risperidone, or quetiapine), anticonvulsant (e.g., benzodiazepine), minocycline, lithium, folic acid, metformin, and a combination thereof. Additionally or alternatively, the human subject may receive an intervention therapy, such as a speech and language therapy, a behavior therapy, a music therapy, a sensory therapy, an occupational therapy, a communication therapy, a reaction therapy, or a diet therapy.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods
PCR Primers

Four sets of PCR primers were synthesized in the present study to detect the CGG repeats of the FMR1 gene. The polynucleotide sequences of the four sets of primers were respectively listed in Tables 1-4.

TABLE 1

The polynucleotide sequences of the first set of PCR primers

| Name | Polynucleotide sequence (from the 5'-end to the 3'end) | SEQ ID NO |
|---|---|---|
| P1 | CGCTCAGCTCCGTTTCGGTTTCACTTCC | 6 |
| P2 | GTAGAAAGCGCCATTGGAGCCCCGCACT | 7 |
| P3 | CTCGACGCACGCTCCTGCACAGCCTCCGGCGGCGGCGG CGG | 8 |
| P4 | CTCGACGCACGCTCCTGCACAGCCTC | 9 |

TABLE 2

The polynucleotide sequences of the second set of PCR primers

| Name | Polynucleotide sequence (from the 5'-end to the 3'end) | SEQ ID NO |
|---|---|---|
| P1 | CGCTCAGCTCCGTTTCGGTTTCACTTCC | 6 |
| P2 | GTAGAAAGCGCCATTGGAGCCCCGCACT | 7 |
| P5 | TGACCGTCTGCGCCTCGTTCCGGCTCGGCGGCGGCGGCGG | 10 |
| P6 | TGACCGTCTGCGCCTCGTTCCGGCT | 11 |

TABLE 3

The polynucleotide sequences of the third set of PCR primers

| Name | Polynucleotide sequence (from the 5'-end to the 3'end) | SEQ ID NO |
|---|---|---|
| P7 | GCACGCTCCTGCACAGCCTCCTCAGCTCCGTTTCGGTT TCACTTCC | 12 |
| P8 | GCACGCTCCTGCACAGCCTCAGCGCCATTGGAGCCCCG CACTTCCA | 13 |
| P3 | CTCGACGCACGCTCCTGCACAGCCTCCGGCGGCGGCGG CGG | 8 |
| P4 | CTCGACGCACGCTCCTGCACAGCCTC | 9 |

TABLE 4

The polynucleotide sequences of the fourth set of PCR primers

| Name | Polynucleotide sequence (from the 5'-end to the 3'end) | SEQ ID NO |
|---|---|---|
| P9 | ACCGTCTGCGCCTCGTTCCGGCTCAGCTCCGTTTCGGT TTCACTTCC | 14 |
| P10 | ACCGTCTGCGCCTCGTTCCGGCTAGCGCCATTGGAGCC CCGCACTTCC | 15 |
| P5 | TGACCGTCTGCGCCTCGTTCCGGCTCGGCGGCGGCGGC GG | 10 |
| P6 | TGACCGTCTGCGCCTCGTTCCGGCT | 11 |

PCR Assay

Four PCR solutions (12.9 μl) respectively comprising the primer sets of Tables 1-4 were mixed with DNA polymerase (0.1 μl) and DNA sample (2 μl), followed by amplifying the DNA molecules of the DNA sample via a PCR process. The components and their concentrations in each PCR solution were summarized in Table 5, and the PCR condition was summarized in Table 6.

TABLE 5

The concentration of specified components of PCR solutions

| Name | PCR solution 1 | PCR solution 2 | PCR solution 3 | PCR solution 4 |
|---|---|---|---|---|
| | Final concentration | | | |
| 10X PCR buffer | 1X | 1X | 1X | 1X |
| 25 mM MgCl$_2$ | 2.5 mM | 2.5 mM | 2.5 mM | 2.5 mM |
| dATP | 0.25 mM | 0.25 mM | 0.25 mM | 0.25 mM |
| dTTP | 0.25 mM | 0.25 mM | 0.25 mM | 0.25 mM |
| dGTP | 0.25 mM | 0.25 mM | 0.25 mM | 0.25 mM |

TABLE 5-continued

The concentration of specified components of PCR solutions

| Name | PCR solution 1 | | PCR solution 2 | | PCR solution 3 | | PCR solution 4 | |
|---|---|---|---|---|---|---|---|---|
| | | | | Final concentration | | | | |
| dCTP | 0.25 mM | | 0.25 mM | | 0.25 mM | | 0.25 mM | |
| Betaine | 1.7M | | 1.7M | | 1.6M | | 1.6M | |
| Ethylene glycol | 0.8M | | 0.8M | | 0.6M | | 0.6M | |
| Glycerol | 4.5% | | 4.5% | | 6.0% | | 6.0% | |
| Primers | P1 | 0.8 μM P1 | | 0.8 μM P7 | | 0.6 μM P9 | | 0.6 μM |
| | P2 | 1.0 μM P2 | | 1.0 μM P8 | | 0.8 μM P10 | | 0.8 μM |
| | P3 | 0.35 nM P5 | | 0.35 nM P3 | | 0.25 nM P5 | | 0.25 nM |
| | P4 | 0.8 μM P6 | | 0.8 μM P4 | | 0.6 μM P6 | | 0.6 μM |

(1) Final volume of each PCR solution: 12.9 μl.
(2) Total reaction volume: 15 μl, including 12.9 μl PCR solution, 1 μl DNA polymerase, and 2 μl DNA sample.

TABLE 6

PCR condition for amplifying DNA fragments
PCR conditions

| | |
|---|---|
| | 95° C./5 minutes |
| 10 cycles | 97° C./35 seconds |
| | 62° C./35 seconds |
| | 68° C./2 minutes |
| 20 cycles | 97° C./35 seconds |
| | 62° C./35 seconds |
| | 68° C./2 minutes + 20 seconds |
| | 72° C./10 minutes |
| | 4° C./overnight |

After the PCR process, 0.5 μl PCR product was mixed with 0.5 μl LIZ® size standard and 9 μl deionized formamide, and analyzed by capillary electrophoresis.

Preparation of Positive Controls

DNA samples isolated from FXS patients were respectively constructed into a TA cloning vector. The thus-produced vectors having 10, 29, 36, 54, 85, 120, 142, and 363 CGG repeats in the polynucleotide sequences thereof were respectively diluted by ddH$_2$O to working concentrations of 0.025, 0.025, 0.025, 0.04, 0.04, 0.05, 0.05, and 0.07 pg/ul.

Construction of Calibration Plot

The vectors respectively comprising 10, 29, 36, 54, 85, 120, 142 CGG repeats were used to construct the calibration plot of the present study. Based on the molecular sizes and CGG repeating numbers of these control vectors, a linear regression formula was established: y=2.9238x+232.4, in which x-value represented the CGG repeating number of the DNA molecule, and y-value represented the molecular size of the DNA molecule. According to the analytic result, the coefficient of determination (i.e., $R^2$) was 1.

Example 1 Evaluation of the Diagnostic Accuracy of the Present Kit 1.1 Positive Reference Samples Twelve positive reference samples was used to evaluate the diagnostic accuracy of the present kit, including, (1) two intermediate samples: the DNA samples isolated from the human subjects respectively having alleles 46/Y (i.e., the male subject having 46 CGG repeats on the X chromosome, and no corresponding allele on the Y chromosome), and alleles 54/Y (i.e., the male subject having 54 CGG repeats on the X chromosome, and no corresponding allele on the Y chromosome);

(2) four permutation samples: the DNA samples isolated from the human subjects respectively having alleles 29/85 (i.e., the female subject having 29 CGG repeats on one X chromosome, and 85 CGG repeats on the other X chromosome), alleles 36/142, alleles 57/Y, and alleles 118/Y;

(3) four full mutation samples: the DNA samples isolated from the human subjects respectively having alleles 30/>200 (i.e., the female subject having 30 CGG repeat on one X chromosome, and more than 200 CGG repeats on the other X chromosome), alleles 29/>200, alleles >200/Y (i.e., the male subject having more than 200 CGG repeats on the X chromosome, and no corresponding allele on the Y chromosome), and alleles >200/Y; and (4) two chimeric mutation samples: the DNA samples isolated from the human subjects respectively having alleles 86>200/Y, and 10>200/Y.

After respectively diluting to concentrations of 2.5, 5, 25, and 50 ng/μl, the positive reference samples were mixed with the PCR solutions for PCR amplification as described in Materials and Methods of the present disclosure. The CGG repeating number in each positive reference sample was then calculated based on the calibration plot. The data indicated that the accuracy of the present kit on determining the CGG repeating number in the positive reference samples was 100% (data not shown).

For the purpose of further evaluating the accuracy of the present kit, different samples were mixed and analyzed by the present kit. According to analytic results, the present kit was capable of identifying the permutation alleles in a mixture containing 1% permutation sample and 39% normal sample, a mixture containing 1% permutation sample and 39% full mutation sample, or a mixture containing 1% permutation sample, 1% full mutation sample and 38% normal sample (data not shown).

1.2 Negative Reference Samples

In addition to the positive reference samples of Example 1.1, the diagnostic accuracy of the present kit was also evaluated by 7 negative reference samples, which were respectively isolated from normal human subjects having alleles 29/29, 30/36, 29/30, 19/30, 30/Y, and 36/Y.

Similarly, the negative reference samples were respectively diluted to concentrations of 5, 25, and 50 ng/μl, and then mixed with the PCR solutions for PCR amplification. The CGG repeating number in each negative reference sample was calculated based on the calibration plot. The data indicated that the accuracy of the present kit on determining the CGG repeating number in the negative reference samples was 100% (data not shown).

1.3 International Standard

World Health Organization (WHO) international standard for FXS was employed as the testing samples in the example. The analytic results were summarized in Table 7.

TABLE 7

Analytic result of WHO international standard by the present kit

| Material | CGG repeats Range | CGG repeats Mean | Diagnostic result |
|---|---|---|---|
| 07/120 | 19-24, 28-33 | 22, 31 | 22, 31 |
| 07/122 | 30-36, 100-132 | 33, 113 | 34, 90, 107, 118, 128 (chimeric alleles) |
| 07/168 | 33-41, 300-401 | 38, 346 | 39, >200 |
| 07/170 | 353-960 | 754 | >200 |
| 07/174 | 97-127 | 114 | 89, 99, 114, 121, 129 (chimeric alleles) |

The data of Table 7 indicated that the present kit may accurately determine the CGG repeating number of the WHO international standard.

Example 2 Determination the CGG Repeating Number of Human Subjects

The whole blood samples were isolated from 120 pregnant women, including 56 normal samples, 14 intermediate samples, 41 premutation samples, and 9 full mutation samples. The DNA samples extracted therefrom were mixed with the present primers, and then processed in accordance with the procedure mentioned in Materials and Methods of the present disclosure. The data was summarized in Table 8.

TABLE 8

Determination of CGG repeats in human subjects by the present kit

| Sample NO. | Allele type | Repeating Number | Diagnostic result |
|---|---|---|---|
| 1 | Normal | 10/32 | 13/32 |
| 2 | Normal | 36/36 | 36/36 |
| 3 | Normal | 29/30 | 29/30 |
| 4 | Normal | 29/40 | 29/40 |
| 5 | Normal | 29/30 | 29/30 |
| 6 | Normal | 22/29 | 22/29 |
| 7 | Normal | 29/36 | 29/36 |
| 8 | Normal | 29/29 | 29/29 |
| 9 | Normal | 29/29 | 29/29 |
| 10 | Normal | 19/30 | 19/30 |
| 11 | Normal | 30/30 | 30/30 |
| 12 | Normal | 29/30 | 29/30 |
| 13 | Normal | 31/36 | 31/36 |
| 14 | Normal | 24/30 | 24/30 |
| 15 | Normal | 29/41 | 29/41 |
| 16 | Normal | 29/29 | 29/29 |
| 17 | Normal | 30/37 | 30/37 |
| 18 | Normal | 31/36 | 31/36 |
| 19 | Normal | 29/29 | 29/29 |
| 20 | Normal | 29/31 | 29/31 |
| 21 | Normal | 29/29 | 29/29 |
| 22 | Normal | 29/30 | 29/30 |
| 23 | Normal | 29/29 | 29/29 |
| 24 | Normal | 34/36 | 34/36 |
| 25 | Normal | 29/36 | 29/36 |
| 26 | Normal | 29/30 | 29/30 |
| 27 | Normal | 29/29 | 29/29 |
| 28 | Normal | 29/30 | 29/30 |
| 29 | Normal | 30/35 | 30/35 |
| 30 | Normal | 29/29 | 29/29 |
| 31 | Normal | 29/30 | 29/30 |
| 32 | Normal | 29/30 | 29/30 |
| 33 | Normal | 29/30 | 29/30 |

TABLE 8-continued

Determination of CGG repeats in human subjects by the present kit

| Sample NO. | Allele type | Repeating Number | Diagnostic result |
|---|---|---|---|
| 34 | Normal | 30/36 | 30/36 |
| 35 | Normal | 29/30 | 29/30 |
| 36 | Normal | 30/32 | 30/32 |
| 37 | Normal | 29/37 | 29/37 |
| 38 | Normal | 30/30 | 30/30 |
| 39 | Normal | 29/36 | 29/36 |
| 40 | Normal | 29/29 | 29/29 |
| 41 | Normal | 30/31 | 30/31 |
| 42 | Normal | 29/37 | 29/37 |
| 43 | Normal | 29/30 | 29/30 |
| 44 | Normal | 29/36 | 29/36 |
| 45 | Normal | 20/29 | 20/29 |
| 46 | Normal | 29/29 | 29/29 |
| 47 | Normal | 29/30 | 29/30 |
| 48 | Normal | 29/36 | 29/36 |
| 49 | Normal | 29/30 | 29/30 |
| 50 | Normal | 29/31 | 29/31 |
| 51 | Normal | 29/31 | 29/31 |
| 52 | Normal | 29/36 | 29/36 |
| 53 | Normal | 15/29 | 15/29 |
| 54 | Normal | 30/36 | 30/36 |
| 55 | Normal | 29/29 | 29/29 |
| 56 | Normal | 29/30 | 29/30 |
| 57 | Intermediate | 51/53 | 51/53 |
| 58 | Intermediate | 23/45 | 23/45 |
| 59 | Intermediate | 30/48 | 30/48 |
| 60 | Intermediate | 29/54 | 29/54 |
| 61 | Intermediate | 36/46 | 36/46 |
| 62 | Intermediate | 29/48 | 29/48 |
| 63 | Intermediate | 22/50 | 22/50 |
| 64 | Intermediate | 36/47 | 36/47 |
| 65 | Intermediate | 29/45 | 29/45 |
| 66 | Intermediate | 31/50 | 31/50 |
| 67 | Intermediate | 30/53 | 30/53 |
| 68 | Intermediate | 54/Y | 54/Y |
| 69 | Intermediate | 30/54 | 30/54 |
| 70 | Intermediate | 29/54 | 29/54 |
| 71 | Premutation | 29/102 | 29/102 |
| 72 | Premutation | 30/69 | 30/69 |
| 73 | Premutation | 36/82 | 36/82 |
| 74 | Premutation | 29/122 | 29/122 |
| 75 | Premutation | 29/86 | 29/86 |
| 76 | Premutation | 61/Y | 61/Y |
| 77 | Premutation | 31/63 | 31/63 |
| 78 | Premutation | 29/70 | 29/70 |
| 79 | Premutation | 30/179 | 30/179 |
| 80 | Premutation | 29/56 | 29/56 |
| 81 | Premutation | 30/81 | 30/81 |
| 82 | Premutation | 29/57 | 29/57 |
| 83 | Premutation | 33/65 | 33/65 |
| 84 | Premutation | 29/81 | 29/81 |
| 85 | Premutation | 29/85 | 29/85 |
| 86 | Premutation | 29/67 | 29/67 |
| 87 | Premutation | 30/77 | 30/77 |
| 88 | Premutation | 29/90 | 29/90 |
| 89 | Premutation | 26/72 | 26/72 |
| 90 | Premutation | 29/98 | 29/98 |
| 91 | Premutation | 30/91 | 30/91 |
| 92 | Premutation | 29/64 | 29/64 |
| 93 | Premutation | 109/Y | 109/Y |
| 94 | Premutation | 29/85 | 29/85 |
| 95 | Premutation | 29/75 | 29/75 |
| 96 | Premutation | 36/142 | 36/142 |
| 97 | Premutation | 29/80 | 29/80 |
| 98 | Premutation | 36/60 | 36/60 |
| 99 | Premutation | 118/Y | 118/Y |
| 100 | Premutation | 29/75 | 29/75 |
| 101 | Premutation | 32/56 | 32/56 |
| 102 | Premutation | 29/102 | 29/102 |
| 103 | Premutation | 36/107 | 36/107 |
| 104 | Premutation | 30/91 | 30/91 |
| 105 | Premutation | 29/60 | 29/60 |
| 106 | Premutation | 29/56 | 29/56 |
| 107 | Premutation | 73/Y | 73/Y |
| 108 | Premutation | 59/Y | 59/Y |
| 109 | Premutation | 68/Y | 68/Y |

TABLE 8-continued

Determination of CGG repeats in human subjects by the present kit

| Sample NO. | Allele type | Repeating Number | Diagnostic result |
|---|---|---|---|
| 110 | Premutation | 31/57 | 31/57 |
| 111 | Premutation | 30/66 | 30/66 |
| 112 | Full mutation | 29/>200 | 29/>200 |
| 113 | Full mutation | >200/Y | >200/Y |
| 114 | Full mutation | 46/>200 | 46/>200 |
| 115 | Full mutation | 36/>200 | 36/>200 |
| 116 | Full mutation | 29/>200 | 29/>200 |
| 117 | Full mutation | 31/>200 | 31/>200 |
| 118 | Full mutation | 30/>200 | 30/>200 |
| 119 | Full mutation | 30/>200 | 30/>200 |
| 120 | Full mutation | 23/>200 | 23/>200 |

Figure 1:
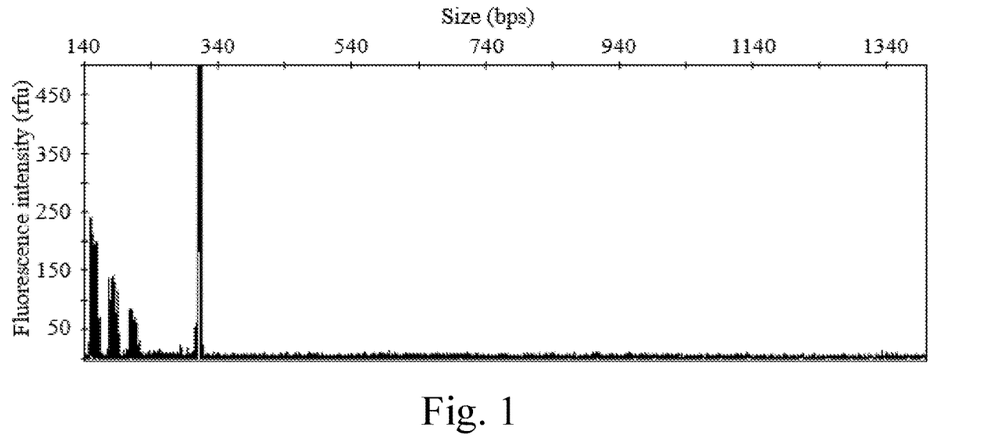
FIG. 1 is an electropherogram depicting the analytic result of DNA sample isolated from a normal female having 29 CGG repeats on one X chromosome, and 30 CGG repeats on the other X chromosome (i.e., having alleles 29/30) according to Example 2 of the present disclosure.
Figure 2:
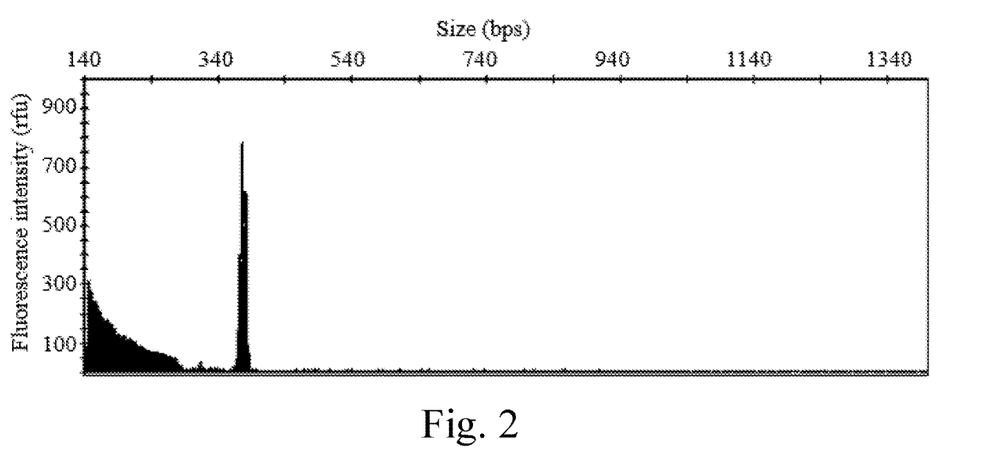
FIG. 2 is an electropherogram depicting the analytic result of DNA sample isolated from an intermediate female having 51 repeats on one X chromosome, and 53 CGG repeats on the other X chromosome (i.e., having alleles 51/53) according to Example 2 of the present disclosure.
Figure 3:
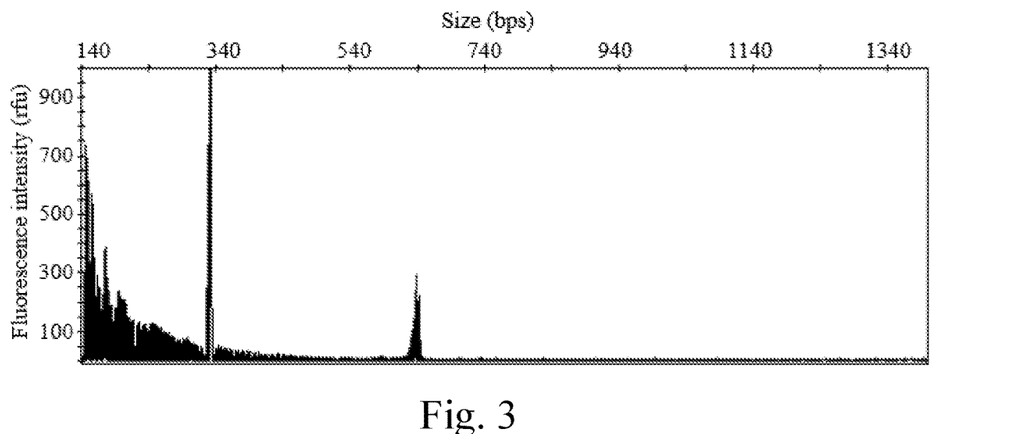
FIG. 3 is an electropherogram depicting the analytic result of DNA sample isolated from a premutation female having 36 repeats on one X chromosome, and 142 CGG repeats on the other X chromosome (i.e., having alleles 36/142) according to Example 2 of the present disclosure.
Figure 4:
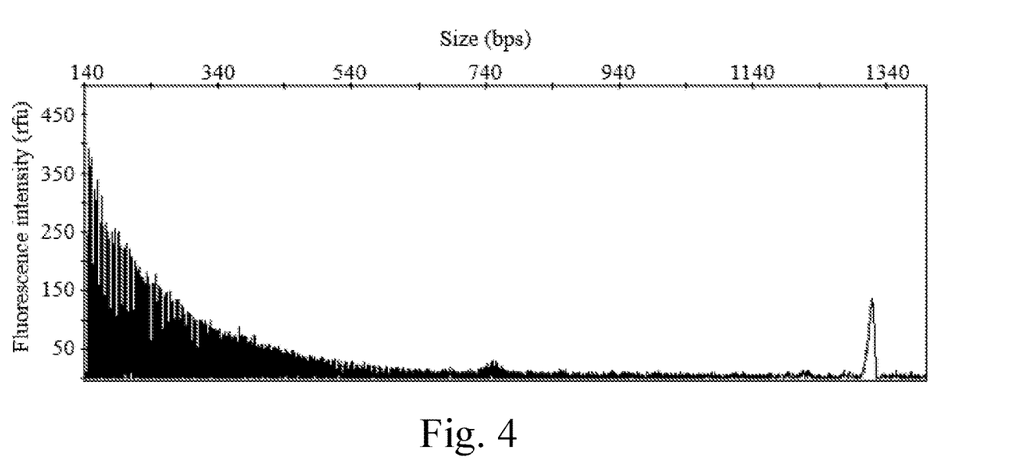
FIG. 4 is an electropherogram depicting the analytic result of DNA sample isolated from a full mutation male having more than 200 repeats on his X chromosome (i.e., having alleles >200/Y, in which Y indicated the Y chromosome) according to Example 2 of the present disclosure.
Figure 5:
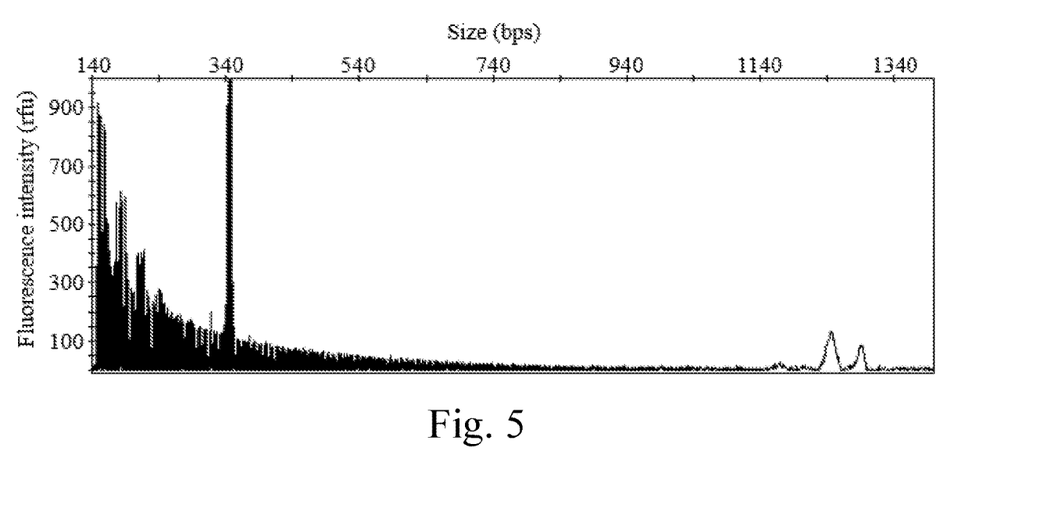
FIG. 5 is an electropherogram depicting the analytic result of DNA sample isolated from a full mutation female having 29 CGG repeats on one X chromosome, and more than 200 repeats on the other X chromosome (i.e., having alleles 29/>200) according to Example 2 of the present disclosure.

The results of electrophoresis assay of DNA samples respectively having alleles 29/30, 51/31, 36/142, >200/Y, and 29/>200 were depicted in FIGS. 1-5, in which the x-coordinate corresponded to the migration time of the DNA sample, and accordingly, the position of each peak on the x-coordinate represented one molecular size; and the y-coordinate corresponded to the relative amount of PCR product of the molecular size. As the data depicted in FIGS. 1 and 2, only one main peak was detected in the electropherogram of DNA samples isolated from normal and intermediate subjects (i.e., 29/30, 51/31). By contrast, in addition to the main peak, the DNA samples isolated from FSX carriers (i.e., 36/142) and FXS patients (i.e., >200/Y, and 29/>200) further exhibited stutter peaks in the electropherogram (FIGS. 3-5).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of performing polymerase chain reaction (PCR) to determine a repeating number of the sequence of CGG in fragile X mental retardation 1 (FMR1) gene by amplifying a CGG repeat region of the FMR1 gene via a first to a fourth primers, wherein
the first primer comprises a first polynucleotide sequence, which is complementary to the upstream sequence of the CGG repeat region;
the second primer comprises a second polynucleotide sequence, which is complementary to the downstream sequence the CGG repeat region;
the third primer comprises a third polynucleotide sequence, and a non-human sequence disposed at and connected to the 5'-end of the third polynucleotide sequence, wherein the third polynucleotide sequence is complementary to the CGG repeat region; and
the fourth primer comprises the non-human sequence; wherein
the first primer consists of the polynucleotide sequence of SEQ ID NO: 12;
the second primer consists of the polynucleotide sequence of SEQ ID NO: 13;
the third primer consists of the polynucleotide sequence of SEQ ID NO: 8; and
the fourth primer consists of the polynucleotide sequence of SEQ ID NO: 9.

2. The method of claim 1, wherein in the PCR, the concentration of the third primer is at least 1,000-fold lower than the concentration of each of the first, second, and fourth primers.

3. A kit for making a diagnosis as to whether a human subject has Fragile X syndrome (FXS) or is a carrier of FXS, comprising,
a first primer consisting of the polynucleotide sequence of SEQ ID NO: 12;
a second primer consisting of the polynucleotide sequence of SEQ ID NO: 13;
a third primer consisting of the polynucleotide sequence of SEQ ID NO: 8;
a fourth primer consisting of the polynucleotide sequence of SEQ ID NO: 9; and polymerase chain reaction (PCR) reagents.

4. The kit of claim 3, wherein the second primer is conjugated with a reporter molecule.

5. The kit of claim 3, further comprising three DNA templates as positive controls, wherein the DNA templates respectively have 10-44, 45-54, and 55-200 repeats of the sequence of CGG within the polynucleotide sequences thereof.

6. The kit of claim 3, further comprising a DNA template as a negative control, wherein the DNA template does not have the sequence of CGG within the polynucleotide sequence thereof.

7. The kit of claim 3, wherein the PCR reagents comprise DNA polymerase, buffer, $MgCl_2$, deoxypolynucleotide triphosphates (dNTPs), betaine, ethylene glycol, and glycerol.

8. A method of making a diagnosis as to whether a human subject has Fragile X syndrome (FXS) or is a carrier of FXS by using the kit of claim 3, comprising, (a) extracting a DNA sample from the human subject;
(b) mixing the DNA sample with the first to fourth primers in the PCR reagents;
(c) subjecting the mixture of the step (b) to PCR;
(d) determining a repeating number of the sequence of CGG in the product of the step (c); and
(e) making a diagnosis of FXS based on the repeating number determined by the step (d), wherein the repeating number of 201-375 indicates that the human subject has the FXS, and the repeating number of 55-200 indicates that the human subject is the carrier of the FXS.

9. The method of claim 8, wherein in the mixture of the step (b), the concentration of the third primer is at least 1,000-fold lower than the concentration of each of the first, second, and fourth primers.

10. The method of claim 9, wherein the concentration of the third primer is 0.1-0.5 nM, and the concentration of each of the first, second, and fourth primers is 0.5-1 μM.

* * * * *